(12) United States Patent
Tatlock

(10) Patent No.: US 7,543,887 B2
(45) Date of Patent: Jun. 9, 2009

(54) SAFETY DENTAL CHAIR

(76) Inventor: Noele R. Tatlock, 407 Kaskaskia Rd., Marquette Heights, IL (US) 61554

( * ) Notice: Subject to any disclaimer, the term of this patent is extended or adjusted under 35 U.S.C. 154(b) by 0 days.

(21) Appl. No.: 11/469,652

(22) Filed: Sep. 1, 2006

(65) Prior Publication Data

US 2008/0122269 A1  May 29, 2008

(51) Int. Cl.
*A47C 7/72* (2006.01)
(52) U.S. Cl. .................................. 297/217.3
(58) Field of Classification Search ............. 297/217.3, 297/397, 452.48; 600/300, 301; 128/920
See application file for complete search history.

(56) References Cited

U.S. PATENT DOCUMENTS

| | | | | |
|---|---|---|---|---|
| 4,541,671 | A * | 9/1985 | Broadhead et al. | 297/330 |
| 4,915,095 | A * | 4/1990 | Chun | 601/43 |
| 5,267,778 | A * | 12/1993 | Krebs et al. | 297/330 |
| 5,320,415 | A | 6/1994 | Krebs | |
| 5,410,471 | A * | 4/1995 | Alyfuku et al. | 600/300 |
| 5,733,010 | A | 3/1998 | Lewis | |
| 6,089,593 | A * | 7/2000 | Hanson et al. | 280/650 |
| 6,163,903 | A * | 12/2000 | Weismiller et al. | 5/610 |
| 6,599,258 | B1 * | 7/2003 | Bystrom et al. | 601/41 |
| 6,652,140 | B1 * | 11/2003 | Taber et al. | 378/177 |
| 6,832,987 | B2 * | 12/2004 | David et al. | 600/300 |
| 6,916,065 | B2 * | 7/2005 | Park | 297/217.1 |
| 2006/0096029 | A1 * | 5/2006 | Osborne et al. | 5/618 |
| 2006/0179571 | A1 * | 8/2006 | Newkirk | 5/600 |
| 2006/0200029 | A1 * | 9/2006 | Evans et al. | 600/485 |
| 2006/0250015 | A1 * | 11/2006 | Buck | 297/397 |

FOREIGN PATENT DOCUMENTS

| | | | |
|---|---|---|---|
| EP | 584439 A1 * | 3/1994 | |
| JP | 03275057 A * | 12/1991 | |
| WO | WO 00/53143 | 9/2000 | |
| WO | WO 01/70169 A1 | 9/2001 | |

* cited by examiner

*Primary Examiner*—David Dunn
*Assistant Examiner*—Patrick Lynch
(74) *Attorney, Agent, or Firm*—Dale J. Ream

(57) ABSTRACT

A safety dental chair includes a chair having a back and seat portions, the back portion having front and rear surfaces and upper and lower ends. The safety dental chair includes an automatic external defibrillator and a CPR safety board removably coupled to the chair back portion adjacent its rear surface. A vitals monitor may also be coupled to the chair which includes a pulse oximetry finger clip, a blood pressure cuff, and at least one display. The vitals monitor includes programming for determining pulse oximetry using data received from the pulse oximetry finger clip, for determining blood pressure using data received from the blood pressure cuff, and for actuating the display to present the oximetry and blood pressure. The safety dental chair may include a headrest constructed of memory foam for supporting a patient's neck and the patient's airway open. The chair may be automated for adjusting its position.

1 Claim, 5 Drawing Sheets

SAFETY DENTAL CHAIR

BACKGROUND OF THE INVENTION

This invention relates generally to medical examination tables and, more particularly, to a dental examination chair equipped to enable quick response to medical emergency conditions of a patient.

Traditional dental examination chairs provide many options for the comfort and convenience of both the patient and the dentist. For example, the chair may be padded as the patient will be lying in it for an extended period of time, sometimes almost entirely in a horizontal position. Further, the chair is typically adjustable to any particular position that is comfortable for the dentist to have access to a patient's mouth. Various dental accessories may be connected to the chair as well, such as a device for spraying water into a patient's mouth or a basin enabling the patient to expel the water.

Dental procedures are sometimes uncomfortable and may result in minor pain or even bleeding of the gums. However, it is possible that more significant medical events may occur while a patient is in the examination chair. Although rare and perhaps unrelated to any dental procedure, a patient may experience a raised pulse or even some degree of heart failure, such as a heart attack. Although the existing dental examination chairs are presumably effective for their intended purposes, they do not provide means for immediately treating the several major medical events that may occur and which may, in a worst case scenario, be fatal.

Therefore, it would be desirable to have a safety dental chair that enables a dentist or dental assistant to provide immediate treatment or analysis of an emergency medical condition. Further, it would be desirable to have a safety dental chair having a vitals monitor for assessing a health situation as well as apparatus for providing emergency and life-saving procedures.

SUMMARY OF THE INVENTION

A safety dental chair according to the present invention includes a chair having a back portion and a seat portion, the back portion having front and rear surfaces and upper and lower ends. The safety dental chair also includes an automatic external defibrillator removably coupled to the chair back portion adjacent its rear surface. A CPR safety board is also removably coupled to the chair back portion adjacent the rear surface. A vitals monitor may also be coupled to the chair that includes a pulse oximetry finger clip, a blood pressure cuff and at least one display. The vitals monitor includes programming for determining pulse oximetry using data received from the pulse oximetry finger clip, for determining blood pressure using data received from the blood pressure cuff and for actuating the display to present the oxinietry and blood pressure. The safety dental chair may also include a headrest constructed of memory foam and situated to support a patient's neck and to keep the patient's airway open. The chair may be automated for adjusting its position.

Therefore, a general object of this invention is to provide a safety dental chair that enables a dentist or technician to respond immediately to an emergency medical event experienced by a patient.

Another object of this invention is to provide a safety dental chair, as aforesaid, that enables the basic vital signs of a patient to be monitored.

Still another object of this invention is to provide a safety dental chair, as aforesaid, that includes a CPR safety board that is immediately available if CPR needs to be administered.

Yet another object of this invention is to provide a safety dental chair, as aforesaid, having an automatic external defibrillator for use in restoring the heart rhythm of a patient who is experiencing cardiac arrest.

A further object of this invention is to provide a safety dental chair, as aforesaid, having a memory foam headrest for maintaining a person's head in a position to keep his airway open in case of an obstruction.

A still further object of this invention is to provide a safety dental chair, as aforesaid, that is comfortable and is adjustable between upright and reclining positions.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 4b is a side view of the safety dental chair as in FIG. 4a;

FIG. 5a is an isolated view on an enlarged scale taken from FIG. 4a; and

DESCRIPTION OF THE PREFERRED EMBODIMENT

A safety dental chair 100 (also referred to herein as a "dental chair system") according to the present invention will now be described in detail with reference to FIGS. 1 through 5b of the accompanying drawings. More particularly, a safety dental chair 100 according to the current invention includes a chair 110.

Figure 1:
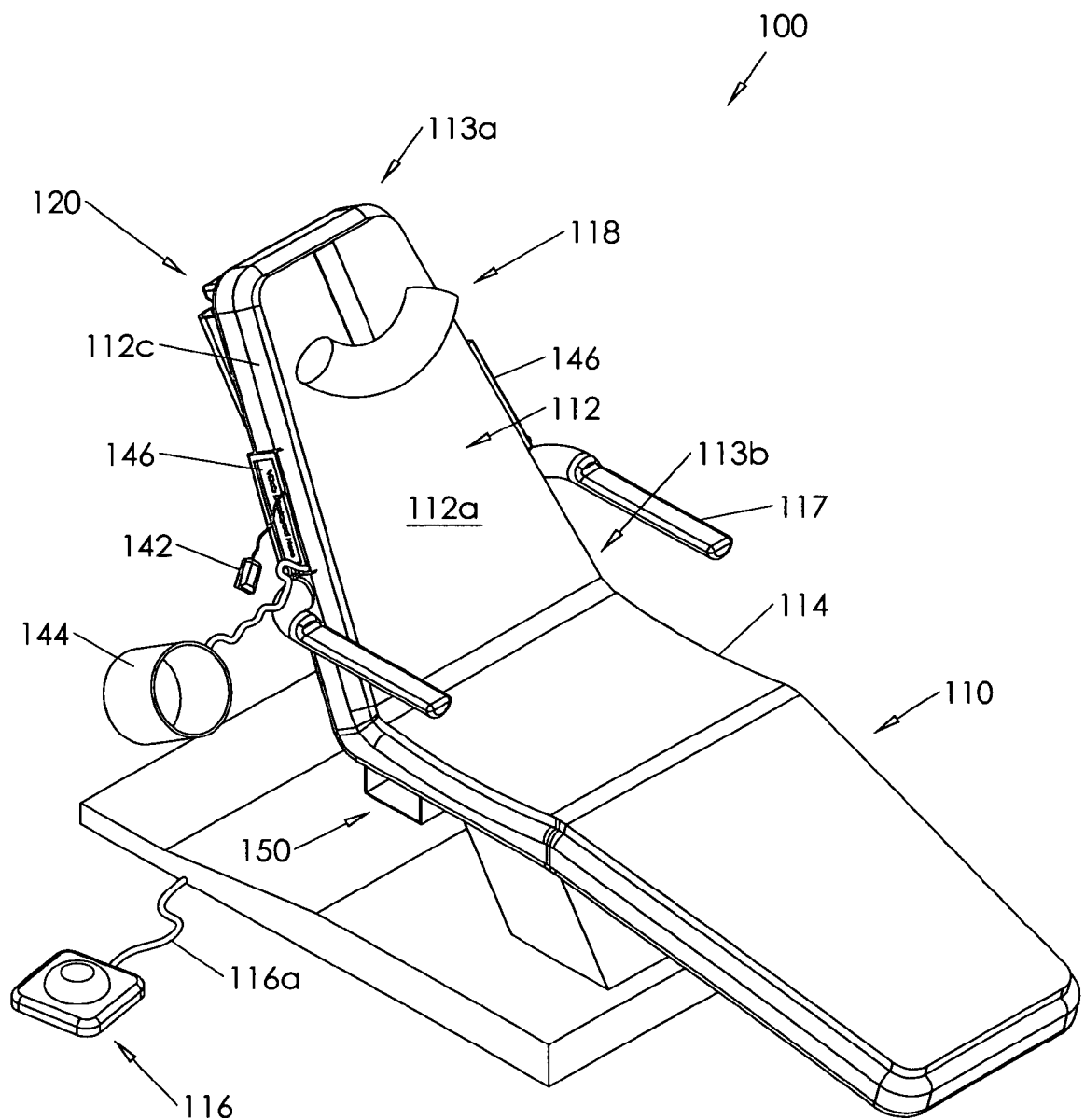
FIG. 1 is a perspective view of a safety dental chair according to a preferred embodiment of the present invention.

The chair 110 has a back portion 112 and a seat portion 114, and the back portion 112 has front and rear surfaces 112a, 112b, opposed sides 112c, and upper and lower ends 113a, 113b. The chair 110 may be an automated chair, meaning that the chair may be movable between various configurations (e.g., sitting up, reclined, etc.), and an input device 116 may be in communication with the automated chair 110 for selectively adjusting the automated chair 110 between the various configurations. The input device 116 may be a foot control as shown in FIG. 1, a hand-operated control, or another type of control. Further, while the input device 116 is shown to be in communication with the chair 110 through wire 116a, the input device and chair 110 may alternately be in wireless communication. The chair 110 may include one or more armrest(s) 117 to support a patient's arm(s), and the armrest(s) 117 may be rotatable to facilitate the patient's entering and leaving the seat portion 114.

A headrest 118 (FIGS. 1 and 2) may be coupled to the chair back portion 112 so that the headrest 118 is located adjacent the upper end 113a and the front surface 112a of the back portion 112 to support the patient's neck and keep the patient's airway open. The headrest 118 may be constructed of memory foam to evenly distribute the pressure on the patient's head and neck, or another material may be used. A mat 119 may be adjacent the chair 110 for comfort (FIG. 2).

Figure 2:
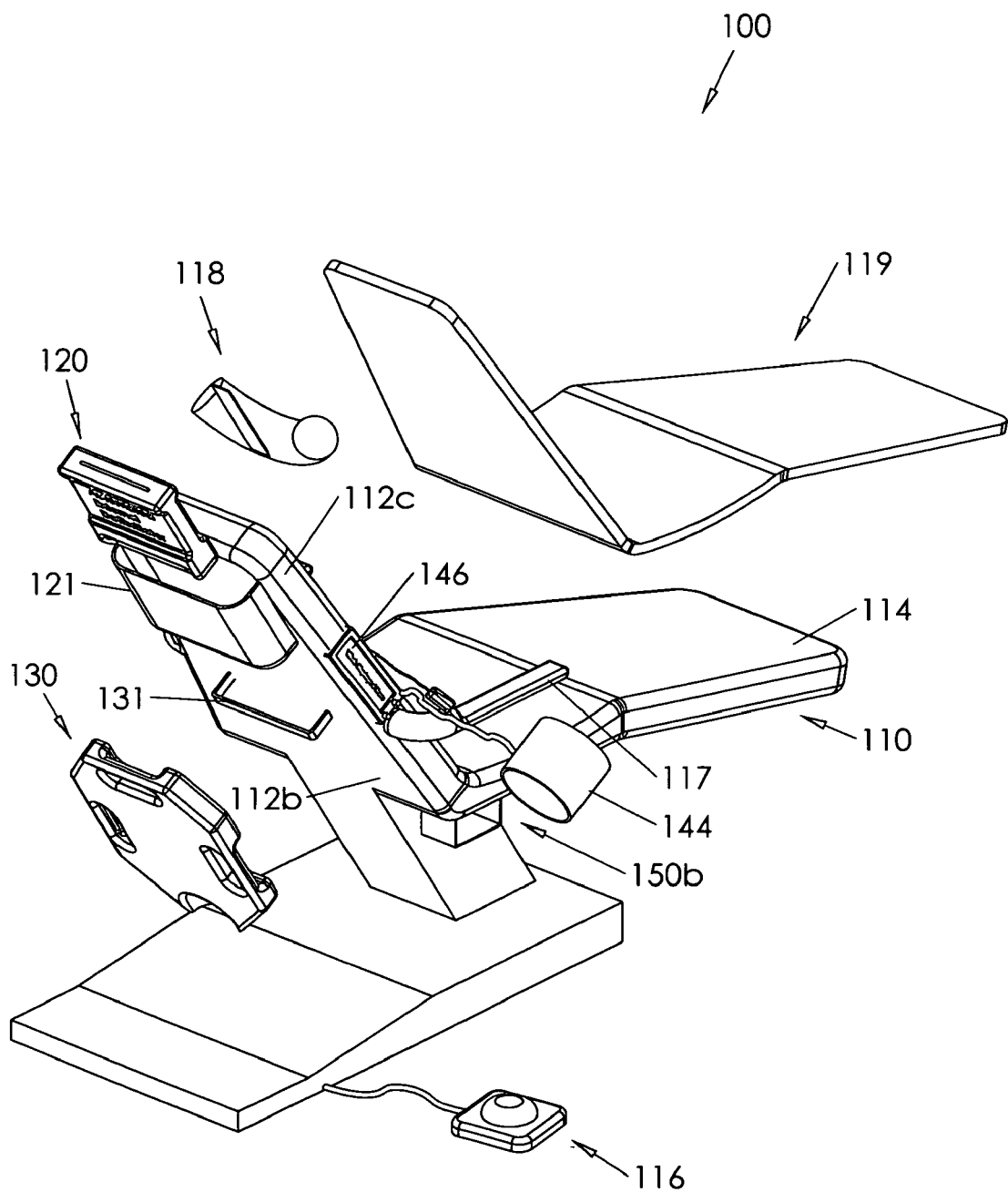
FIG. 2 is an exploded view of the safety dental chair as in FIG. 1 taken from an other angle.
Figure 3A:
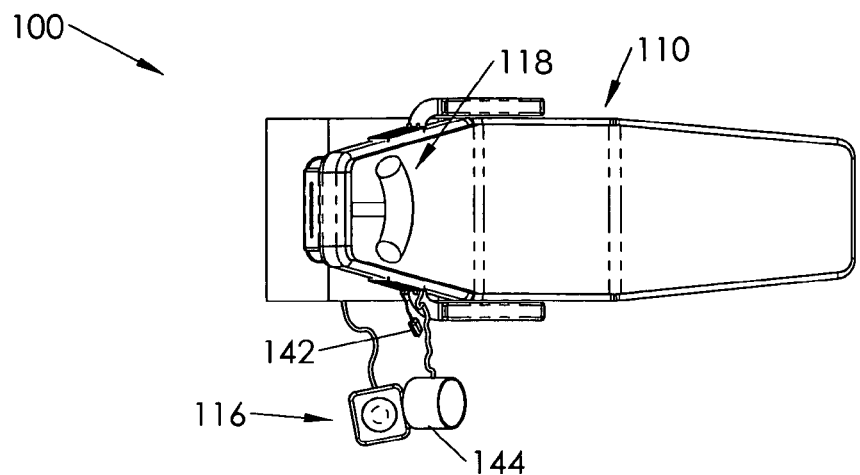
FIG. 3a is a top view of the safety dental chair as in FIG. 1.
Figure 3B:
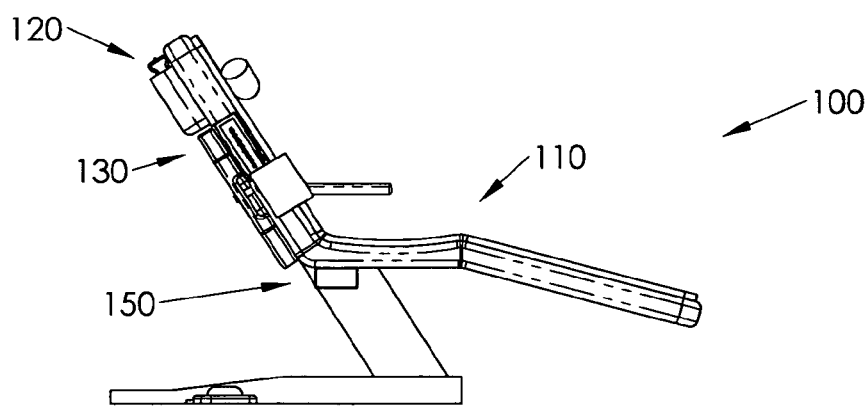
FIG. 3b is a side view of the safety dental chair as in FIG. 1.
Figure 3C:
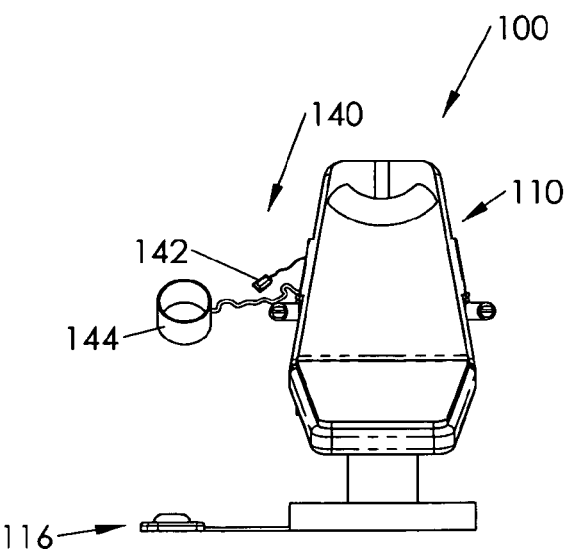
FIG. 3c is a front view of the safety dental chair as in FIG. 1.
Figure 4A:
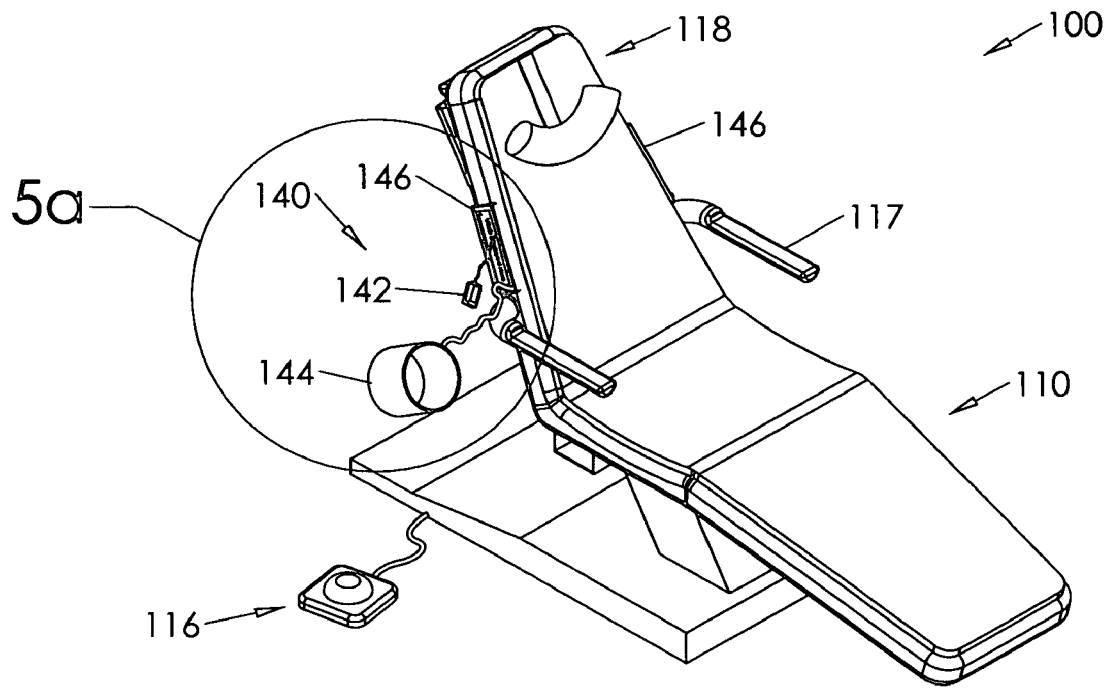
FIG. 4a is another perspective view of the safety dental chair.
Figure 4B:
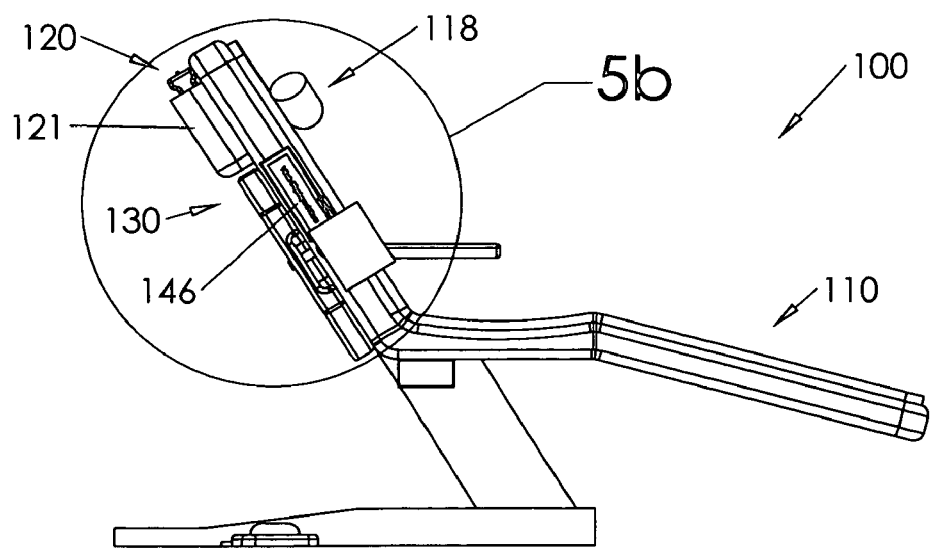

As shown in FIGS. 1, 2, 3b, 4b, and 5b, an automatic external defibrillator 120 may be removably coupled to the chair back portion 112 adjacent the rear surface 112b. An automatic external defibrillator is a portable automatic device used to restore normal heart rhythm to patients in cardiac arrest. It is applied outside the body and automatically analyzes the patient's heart rhythm and advises a rescuer whether or not a shock is needed to restore a normal heart beat. When necessary, the automatic external defibrillator delivers an electric shock that stuns the heart momentarily, stopping all heart activity. This stop in heart activity gives the heart a chance to restart normal electrical activity and resume beating effectively. As shown in FIG. 2, a pocket 121 may be attached to or formed by the chair 110, and the automatic external defibrillator 120 may be contained in the pocket 121. Alternately, hook and loop fasteners or other fastening devices may selectively couple the automatic external defibrillator to the chair back portion 112.

As shown in FIGS. 2, 3b, 4b, and 5b, a CPR safety board 130 may be removably coupled to the chair back portion 112 adjacent the rear surface 112b. A CPR safety board is a board that can be slid beneath a patient in need of CPR (cardiopulmonary resuscitation) to help keep the patient in a proper position to receive CPR. For example, the CPR safety board 130 may hold the patient's head back to keep the airway open and provide a stable surface for chest compressions. As shown in FIG. 2, hook and loop fasteners 131 may selectively couple the CPR safety board 130 to the chair back portion 112. Alternately, a pocket may be attached to or formed by the chair 110 for containing the CPR safety board 130, or other fastening devices may be used.

Figure 5A:
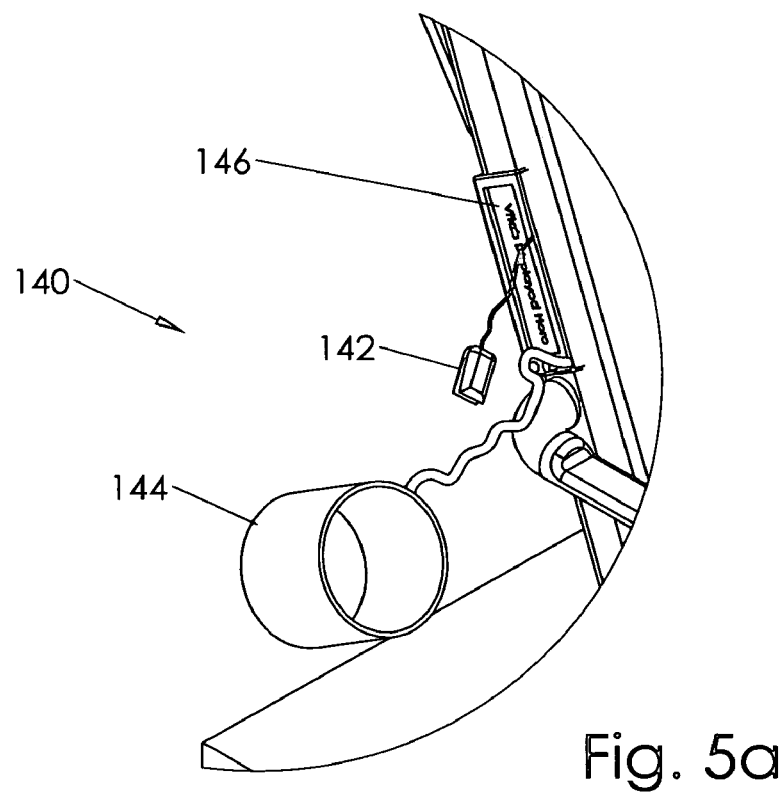
Figure 5B:
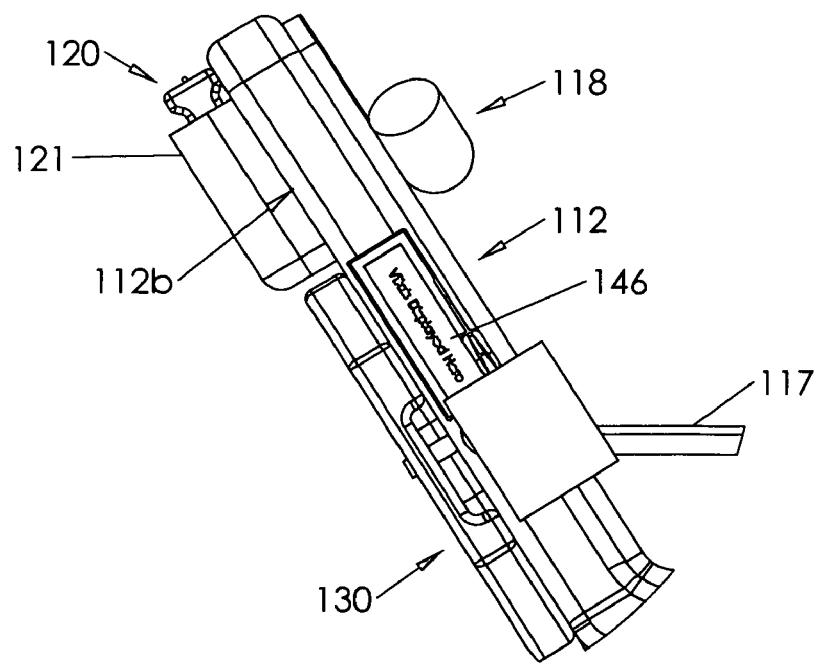
FIG. 5b is an isolated view on an enlarged scale taken from FIG. 4b.

Means for monitoring vital signs of a patient sitting in the chair 110 may be included. More particularly, a vitals monitor 140 may be coupled to the chair 110. The vitals monitor 140 may include, for example, a pulse oximetry finger clip 142, a blood pressure cuff 144, at least one display 146, a thermometer, and/or electrocardiogram electrodes. At least one respective display 146 may be coupled to a respective side 112c of the chair back portion 112, as shown in FIGS. 1, 2, and 5b. The vitals monitor 140 may include programming for determining pulse oximetry using data from the pulse oximetry finger clip 142, programming for determining blood pressure using data from the blood pressure cuff 144, programming for determining information regarding a heart's electrical activity using data from the electrocardiogram electrodes, and/or programming for actuating the at least one display 146 to present the pulse oximetry, the blood pressure, and/or the information regarding the heart's electrical activity. A container 150 may be coupled to the chair 110, such as below the seat portion 114 as shown in FIGS. 1 and 2, and the pulse oximetry finger clip 142, the blood pressure cuff 144, and/or the input device 116 may be separable from the chair 110 and positionable in the container 150 for storage.

In use, a respective armrest 117 may be rotated to allow a patient to sit down on the chair seat portion 114, the patient may sit down on the chair seat portion 114, and the armrest 117 may be rotated back to support one of the patient's arms. The patient may lean back against the chair back portion 112, and the headrest 118 may support his neck and keep his airway open. The input device 116 may be used to move the chair 110 from an upright configuration to a reclined configuration as discussed above. The pulse oximetry finger clip 142 may be placed on one of the patient's fingers, the pressure cuff 144 may be placed about one of the patient's arms, and a dentist, hygienist, or other person may monitor the display(s) 146 for information as discussed above. If necessary, the automatic external defibrillator 120 may be separated from the chair 110 and used to restart normal electrical activity of the patient's heart. Similarly, the CPR safety board 130 may be separated from the chair 110 and used in administering CPR if necessary. The information provided by the display(s) 146, the easy access to the automatic external defibrillator 120, and/or the easy access to the CPR safety board 130 may be life-saving.

It is understood that while certain forms of this invention have been illustrated and described, it is not limited thereto except insofar as such limitations are included in the following claims and allowable functional equivalents thereof.

What is claimed is as follows:

1. A safety dental chair for treating a dental patient, comprising:
    a dental chair having a back portion and a seat portion, said back portion having front and rear surfaces and upper and lower ends;
    a vitals monitor coupled to said chair, said vitals monitor having a pulse oximetry finger clip, a blood pressure cuff, at least one display, programming for determining pulse oximetry using data from said pulse oximetry finger clip, programming for determining blood pressure using data from said blood pressure cuff, and programming for actuating said at least one display to present said pulse oximetry and said blood pressure;
    wherein said chair back portion includes a pocket on the rear surface of the back portion;
    wherein:
        said chair is an automated chair;
        an input device is in communication with said automated chair for selectively adjusting a configuration of said automated chair;
    a container coupled to said chair beneath said seat portion;
    wherein at least one item selected from said pulse oximetry finger clip, said blood pressure cuff, and said input device is separable from said chair and positionable in said container;
    an automatic external defibrillator housed within and removable from said pocket on the rear surface of the back portion;
    a CPR safety board removably coupled to said chair back portion adjacent said rear surface;
    wherein:
        said back portion of said chair has opposed sides;
        said at least one display is directly coupled to one of said opposed sides of said chair back portion and faces in a direction that is away from the chair back portion and opposite the other of said opposed sides;
    a headrest constructed of memory foam, said headrest being coupled to said chair back portion and being located adjacent said upper end of said front surface of said back portion to support a patient's neck and keep the patient's airway open.

* * * * *